United States Patent [19]

Willersinn

[11] Patent Number: 5,426,221
[45] Date of Patent: Jun. 20, 1995

[54] SEPARATION OF ACRYLIC ACID FROM THE REACTION GASES FROM THE CATALYTIC OXIDATION OF PROPYLENE AND/OR ACROLEIN

[75] Inventor: Carl-Heinz Willersinn, Ludwigshafen, Germany

[73] Assignee: BASF Aktiengesellschaft, Ludwigshafen, Germany

[21] Appl. No.: 202,562

[22] Filed: Feb. 28, 1994

[30] Foreign Application Priority Data

Mar. 13, 1993 [DE] Germany .................. 43 08 087.1

[51] Int. Cl.⁶ .............................................. C07C 51/42
[52] U.S. Cl. ................................................... 562/600
[58] Field of Search ........................................ 562/600

[56] References Cited

FOREIGN PATENT DOCUMENTS 2136396 2/1973 Germany .
2241714 3/1974 Germany .
2449780 4/1976 Germany .

*Primary Examiner*—Paul J. Killos
*Attorney, Agent, or Firm*—Oblon, Spivak, McClelland, Maier, & Neustadt

[57] ABSTRACT

A process for the separation of acrylic acid from the reaction gases from the catalytic oxidation of propylene and/or acrolein by countercurrent absorption using a mixture of from 70 to 75 wt % of diphenyl ether and from 25 to 30 wt % of diphenyl plus from 0.1 to 25 wt % of o-dimethyl phthalate, based on said mixture.

1 Claim, No Drawings

SEPARATION OF ACRYLIC ACID FROM THE REACTION GASES FROM THE CATALYTIC OXIDATION OF PROPYLENE AND/OR ACROLEIN

The present invention relates to a novel process for the separation of acrylic acid from the reaction gases from the catalytic oxidation of propylene and/or acrolein by countercurrent absorption using a high-boiling liquid whilst avoiding the occurrence of an aqueous phase, comprising cooling the reaction gases to the desired absorption temperature on leaving the oxidation stage, passing them through an absorption column countercurrently to the descending high-boiling liquid, removing readily volatile minor constituents from the acrylic acid-containing liquid effluent of the absorption column in a desorption column by stripping, treating the liquid effluent of the desorption column by distillation and if necessary by extraction with water in order to separate substantially pure acrylic acid and more difficultly volatile minor constituents, and recycling very difficultly volatile residues, consisting mainly of the high-boiling liquid, to the absorption column for further absorption.

Acrylic acid forms, on account of its very reactive double bond and its acid nature, a valuable monomer for the preparation of polymers, eg, for aqueous polymer dispersions suitable for use as adhesives.

Acrylic acid can be prepared, inter alia, by gas phase oxidation of propylene and/or acrolein with oxygen or gases containing oxygen in the presence of catalysts (oxides of the elements molybdenum, chromium, vanadium, tellurium) at elevated temperature and, preferably, on account of the high heat of reaction, with dilution of the reactants with inert gases and/or steam. This process, however, does not produce pure acrylic acid, but a gas mixture, which contains, in addition to acrylic acid, minor constituents comprising substantially unconverted acrolein and/or propylene, steam, carbon oxides, nitrogen, oxygen, acetic acid, formaldehyde and maleic anhydride, from which mixture the acrylic acid must be subsequently separated.

DE-PS 2,136,396 reveals that it is possible to separate acrylic acid from the reaction gases coming from the catalytic oxidation of propylene and/or acrolein by countercurrent absorption using a mixture of 75% wt % of diphenyl ether and 25% wt % of diphenyl whilst avoiding the occurrence of an aqueous phase. Essentially, the process is carried out in such a manner that the reaction gases are cooled to the desired absorption temperature on leaving the oxidation stage and are passed through an absorption column countercurrently to the descending mixture of diphenyl ether and diphenyl, after which the readily volatile secondary constituents are substantially removed from the liquid effluent from the absorption column, which is substantially composed of acrylic acid, the absorbent and (in minor quantities) secondary constituents, in a desorption column by stripping, followed by treating the liquid effluent of the desorption column by distillation and optionally by extraction with water for the purpose of separating substantially pure acrylic acid and difficultly volatile secondary constituents, and recycling the resulting very difficultly volatile residue mainly consisting of diphenyl ether/diphenyl to the absorption column for further absorption.

One important advantage of this process is that the cooling of the reaction gases coming from the oxidation stage and having a temperature of from 200° to 300° C. to the absorption temperature can be effected in an advantageous manner by direct contact with the absorbents comprising diphenyl ether and diphenyl. This process suffers from the drawback that despite the use of stabilizers for acrylic acid virtually non-vaporizable polymers are formed, which accumulate in the diphenyl ether/diphenyl mixture together with other virtually non-vaporizable impurities and form deposits in the different constituent parts of the plant, eg, in the absorption column or the heat exchangers, during circulation therethrough. This eventually leads, for example, to pressure losses and to a reduction in heat transfer, which makes it necessary to shut down and clean the plant when a certain limit has been reached, eg, when the absorption column becomes choked up, if not before. In order to increase the on-stream times of the plant, DE-PS 2,136,396 proposes the purification of a partial stream of the absorbent to remove the virtually non-vaporizable impurities, which can be effected in a simple manner by distilling off the absorbent, or which can be carried out according to the teaching of DE-PS 2,449,780. DE-AS 2,241,714 and DE-A 1,568,937 refer to a similar process to that described in DE-PS 2,136,396 for the separation of acrylic acid from the reaction gases from the catalytic oxidation of propylene and/or acrolein, in which o-diethyl phthalate is used as high-boiling absorbent, and it is again recommended to remove the very high-boiling impurities from the circuit during circulation of the o-diethyl phthalate.

A drawback of this process, compared with the method using diphenyl ether/diphenyl as described in DE-PS 2,136,396, is, on the one hand, that the higher boiling-point of the o-diethyl phthalate involves an increase in energy consumption during removal, by distillation, of the acrylic acid and that on the other hand cooling of the reaction gases coming from the oxidation stage and having a temperature of from 200° to 300° C. to the absorption temperature by direct contact with the absorbent o-diethyl phthalate causes thermal decomposition of the latter, which usually gives rise to a transesterification reaction involving the acrylic acid and thus leads to a loss of desired product.

It is therefore an object of the present invention to provide a process for the separation of acrylic acid from the reaction gases from the catalytic oxidation of propylene and/or acrolein by countercurrent absorption using a high-boiling liquid with circulation thereof, which process A) has no appreciably greater energy requirements than the process using diphenyl ether/diphenyl described in DF-PS 2,136,396, B) makes it possible to cool the reaction gases coming from the oxidation stage and having a temperature of from 200° to 300° C. to the absorption temperature by direct contact with the absorbent without the occurrence of any appreciably greater loss of desired product as compared with the process using diphenyl ether/diphenyl described in DE-PS 2,136,396 and C) makes increased on-stream periods possible without removal of the virtually non-vaporizable impurities from the circuit during circulation of the high-boiling absorbent.

Accordingly, we have found a process for the separation of acrylic acid from the reaction gases from the catalytic oxidation of propylene and/or acrolein by countercurrent absorption using a high-boiling liquid whilst avoiding the occurrence of an aqueous phase, comprising cooling the reaction gases to the desired absorption temperature on leaving the oxidation stage, passing them through an absorption column countercurrently to the descending high-boiling liquid, removing readily volatile secondary constituents from the acrylic acid-containing liquid effluent of the absorption column in a desorption column by stripping, treating the liquid effluent of the desorption column by distillation and if necessary by extraction with water in order to separate substantially pure acrylic acid and more difficultly volatile secondary constituents, and recycling very difficultly volatile residues, consisting mainly of the high-boiling liquid, to the absorption column for further absorption, wherein the high-boiling liquid used for the countercurrent absorption is a mixture of from 70 to 75 wt % of diphenyl ether and from 25 to 30 wt % of diphenyl plus from 0.1 to 25 wt % of o-dimethyl phthalate, based on said mixture. Preferably, the diphenyl ether/diphenyl mixture has the composition 73.5:26.5 wt % and the content of o-dimethyl phthalate in the absorbents is from 15 to 20 wt %. In order to avoid the occurrence of an aqueous phase during absorption, pressure and temperature used in the process of the invention are governed by the water content of the reaction gases, whilst excessively high temperatures are undesirable in that they reduce the uptake of the acrylic acid in the absorbent.

Depending on the content of water vapor in the reaction gases coming from the catalytic oxidation, the most favorable absorption temperature is, under standard pressure, between approximately 30° and 80° C. Cooling of the reaction gases to the absorption temperature can be carried into effect by indirect cooling in heat exchangers. However, it is preferably carried out in a gas condenser by direct contact with the high-boiling absorbent, which is reseparated as far as possible in a trap prior to entering the absorption column, after which it is advantageously recycled to the gas condenser.

The amount of high-boiling liquid used in the absorption column is usually such that the bottom product of the absorption column contains approximately from 6 to 15 wt % of acrylic acid. The maximum content possible depends on the absorption temperature, the dimensions of the absorption column, and the desired absorption yield. The absorption column used can be, inter alia, a packed column, a valve-tray column, or a bubble-cap column. The bottom product of the absorption column contains, in addition to acrylic acid, normally less than 5 wt % of water, traces of acrolein and formaldehyde, and small amounts of acetic acid and maleic anhydride.

The residual water, the traces of acrolein and formaldehyde, and the acetic acid are substantially removed in a down-stream desorption column by stripping, in which the countercurrent stripping gas used can be, eg, nitrogen or air. The stripping gas rate required for this purpose primarily depends on the desorption temperature, which is advantageously set at from 20° to 50° C. higher than the absorption temperature, at the same pressure. In this case, the stripping gas rate required in order to obtain a bottom product of the desorption column which is virtually free from water, is, based on the reaction gas rate, from 5 to 25 percent by volume. The desorption column can be, like the absorption column, eg, a packed column, a valve-tray column, or a bubble-cap column. Purification of the bottom product of the desorption column is conveniently made dependent on whether it still contains low-boiling components such as acetic acid or not. If the absorption and desorption conditions are selected such that the low-boiling fractions such as acetic acid are removed without the use of additional measures, it will be possible to isolate, by distillation, substantially pure acrylic acid from the bottom product of the desorption column directly (the purity is usually about 99 wt %).

If the bottom product of the desorption column still contains, eg, a small amount of acetic acid, it will be advantageous to remove this, by distillation, prior to the isolation of the acrylic acid from the bottom product of the desorption column.

Some or all of the secondary constituents which are less volatile than acrylic acid, such as maleic anhydride, are advantageously separated from the bottom product of the desorption column immediately following the separation of the acrylic acid and prior to recycling. This can be effected, for example, by distillation or alternatively by extraction with water.

In some cases, it will be advantageous to heat treat the residue mainly consisting of the high-boiling absorbent before recycling it to the absorption column, at temperatures exceeding 180° C., during which process impurities contained therein and comprising ester-like oligomeric acrylic acids are decomposed and the acrylic acid formed is removed by distillation. In all of the purifying stages, stabilizers for acrylic acid, eg, phenothiazine, are added in known manner. Surprisingly, the process of the invention effects a distinct prolongation of the on-stream period.

A further prolongation of the on-stream period can be achieved by separating the virtually non-vaporizable impurities from a partial stream tapped from the circulating high-boiling absorbent.

Example B and Comparative Example V a)
V: 2.1 m$^3$/h(S.T.P.) of reaction gas, which contained 4.1 vol % of acrylic acid, 0.21 vol % of acetic acid, 0.15 vol % of formaldehyde, 0.05 vol % of acrolein, 6.9 vol % of steam, 0.025 vol % of maleic anhydride, the remainder being substantially inert gases such as $N_2$, $CO_2$, CO and propylene, was cooled from 250° to 170° C. in a gas condenser by injecting a coolant mixture of 73.5 wt % of diphenyl ether and 26.5 wt % of diphenyl. Then, in a trap, the still liquid portion of the coolant was removed from the gas phase consisting of reaction gas and vaporized absorbent and recycled to the gas condenser in a circuit I. The gas phase having a temperature of 170° C. was introduced below the first plate of a bubble-cap column having 27 plates of 80 mm in diameter and was thus exposed to a countercurrent of 3 L/h of the absorbent fed to the head of the column while having a temperature of 45° C. and likewise consisting of 73.5 wt % of diphenyl ether and 26.5 wt % of diphenyl. The bottom product of the absorption column was indirectly heated to 105° C. in a heat exchanger and fed to the top of a desorption column, which was a bubble-cap column having 20 plates. In the desorption column, the components which are more volatile than acrylic acid such as acrolein and acetic acid were substantially removed from the acrylic acid/absorbent mixture by stripping with nitrogen (400 L/h, countercurrently). The bottom product of the desorption column was passed to the middle portion of a rectifying column containing 35 bubblecap plates. In the rectifying column, the acrylic acid was separated, by distillation, it vacuo, as overheads exhibiting a purity of 98.5 wt %. The main portion (ca 90 wt %) of the bottom product of the rectifying column was directly fed to the head of the absorption column. The residual amount of the bottom product of the rectifying column (ca 10 wt %) was added to the aforementioned circuit I following distillative separation of maleic anhydride, by which means losses due to evaporation resulting from the said direct cooling were compensated. Furthermore, the non-volatile impurities occurring as distillation residue were separated from 2 wt % of the circuit I continuously by simple distillation, and the distillate was recycled to the circuit I.

At commencement, the pressure loss incurred via the absorption column was 176 mbar. After 1815 hours of operation, the pressure loss was 383 mbar.

B: Example V, a), was repeated except that a mixture of 57.4 wt % of diphenyl ether, 20.7 wt % of diphenyl, and 20 wt % of o-dimethyl phthalate was used both to precool the reaction gases and to act as absorption liquid. Acrylic acid containing 0.26 wt % of acetic acid and 0.04 wt % of water was obtained.

At commencement, the pressure loss across the absorption column was 174 mbaro. This value remained constant over an on-stream period of 7790 h.

b) Example a) was repeated except that a partial stream of 1.5 L/h of the immediate bottom product of the rectifying column was passed, before recycling it to the absorption column, through a column of 20 mm in diameter, which contained a layer of high-grade steel rings (3.3 mm), for the purpose of separating the virtually non-vaporizable impurities, this being continued until the throughput of 1.5 L/h could no longer be maintained by further increases in pressure. When using a mixture of 73.5 wt % of diphenyl ether and 26.5 wt % of diphenyl as high-boiling liquid, this point was reached after a period of 62 h (V, b). When using mixtures of o-dimethyl phthalate and the 73.5:26.5 wt % diphenyl ether/diphenyl mixture, the following on-stream periods were achieved as a function of the content of o-dimethyl phthalate.

| (B, b): | |
|---|---|
| wt % of o-Dimethyl Phthalate | On-stream Period (h) |
| 15.5 | 750 |
| 12.4 | 498 |
| 5.8 | 328 |
| 0.11 | 204 |

We claim:

1. A process for the separation of acrylic acid from the reaction gases from the catalytic oxidation of propylene and/or acrolein by countercurrent absorption using a high-boiling liquid whilst avoiding the occurrence of an aqueous phase, comprising cooling the reaction gases to the desired absorption temperature on leaving the oxidation stage, passing them through an absorption column countercurrently to the descending high-boiling liquid, removing readily volatile secondary constituents from the acrylic acid-containing liquid effluent of the absorption column in a desorption column by stripping, treating the liquid effluent of the desorption column by distillation and if necessary by extraction with water in order to separate substantially pure acrylic acid and more difficultly volatile secondary constituents, and recycling very difficultly volatile residues, consisting mainly of the high-boiling liquid, to the absorption column for further absorption, wherein the high-boiling liquid used for the countercurrent absorption is a mixture of from 70 to 75 wt % of diphenyl ether and from 25 to 30 wt % of diphenyl plus from 0.1 to 25 wt % of o-dimethyl phthalate, based on said mixture.

* * * * *